US006416993B1

(12) United States Patent
Wexler et al.

(10) Patent No.: US 6,416,993 B1
(45) Date of Patent: *Jul. 9, 2002

(54) METHOD FOR TREATING A WASTE STREAM USING PHOTOSYNTHETIC MICROORGANISMS

(75) Inventors: Howard M. Wexler, 32 Summer Glen, Bristol, CT (US) 06010; Joseph F. Startari, Clearwater, FL (US)

(73) Assignees: Biotechna Environmental International, Ltd. (KN); Howard M. Wexler, Bristol, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/263,040

(22) Filed: Mar. 5, 1999

Related U.S. Application Data

(63) Continuation-in-part of application No. 09/210,153, filed on Dec. 11, 1998.

(51) Int. Cl.⁷ .............................. B09B 3/00; C12N 1/00; C12N 1/20
(52) U.S. Cl. ................ 435/262.5; 435/243; 435/252.1; 435/257.1; 435/289.1; 435/822; 210/601; 210/602
(58) Field of Search ................. 435/262.5, 822, 435/243, 252.1, 289.1; 210/601, 602

(56) References Cited

U.S. PATENT DOCUMENTS

| | | | |
|---|---|---|---|
| 2,715,795 A | 8/1955 | Pallotta et al. ........... 47/58 |
| 3,955,318 A | 5/1976 | Hulls .................... 47/1.4 |
| 4,016,079 A | 4/1977 | Severin ................. 210/96 R |
| 4,267,038 A | 5/1981 | Thompson .............. 210/602 |
| 4,267,826 A | 5/1981 | Hitt, Jr. ................ 126/440 |
| 4,321,141 A * | 3/1982 | Messing ................. 210/603 |
| 4,348,285 A | 9/1982 | Groeneweg ............. 210/602 |
| 4,432,869 A | 2/1984 | Groeneweg ............. 210/602 |
| 4,550,011 A | 10/1985 | McCollum ............... 422/68 |
| 4,793,929 A | 12/1988 | Kickuth et al. .......... 210/602 |
| 4,868,123 A | 9/1989 | Berson et al. ........... 435/290 |
| 4,952,511 A | 8/1990 | Radmer ................. 435/314 |
| 5,078,882 A | 1/1992 | Northrop ............... 210/602 |
| 5,087,353 A * | 2/1992 | Todd et al. .............. 210/94 |
| 5,137,828 A | 8/1992 | Robinson et al. ........ 435/296 |
| 5,162,051 A | 11/1992 | Hoeksema .............. 47/1.4 |
| 5,389,257 A * | 2/1995 | Todd et al. ............. 210/602 |
| 5,447,629 A | 9/1995 | Chaumont et al. ...... 210/96.1 |
| 5,472,472 A | 12/1995 | Northrop ................ 71/9 |
| 5,538,529 A | 7/1996 | Northrop ................ 71/9 |
| 5,626,644 A | 5/1997 | Northrop ................ 71/9 |
| 5,755,852 A | 5/1998 | Northrop ................ 71/9 |
| 5,795,480 A | 8/1998 | Keun et al. ............. 210/611 |

OTHER PUBLICATIONS

Animal Waste Pollution in America: An Emerging National Problem, Senate Report, Dec., 1997.

* cited by examiner

Primary Examiner—David M. Naff
Assistant Examiner—Deborah K Ware
(74) Attorney, Agent, or Firm—Todd E. Garabedian; Wiggin & Dana

(57) ABSTRACT

The present invention is directed to a method for treating a waste stream by contacting the waste stream sequentially with a consortium of prokaryotic microorganisms, preferably purple non-sulfur bacteria, followed by a the green algae Chlorella. The consortium of prokaryotic microorganisms assimilate a first portion of the wastes, and the green algae assimilate the remaining portion of the wastes to produce a substantially purified effluent stream. The process of the present invention preferably includes a photobioreactor in order to increase the amount of light made available to the photosynthetic microorganisms, and result in improved uptake of waste materials from the waste stream.

39 Claims, 5 Drawing Sheets

A B C

US 6,416,993 B1

METHOD FOR TREATING A WASTE STREAM USING PHOTOSYNTHETIC MICROORGANISMS

CROSS-REFERENCE TO RELATED APPLICATIONS

This application is a continuation-in-part of U.S. application Ser. No. 09/210,153, filed Dec. 11, 1998.

BACKGROUND OF THE INVENTION

1. Field of the Invention

This invention relates to purification systems for wastes, and more particularly to purification systems for agricultural and livestock waste that utilize photosynthetic microorganisms in a photobioreactor to biodegrade and remove organic and inorganic matter.

2. Description of the Related Art

Over the past few decades, there has been an exponential increase in the human population accompanied by a concomitant increase in the demand for cattle, poultry, fish and other livestock and agricultural products. However, the increased demand for agricultural and livestock products necessarily results in an increased amount of agricultural and livestock waste. In addition, the rise in industrial farming, wherein livestock are concentrated in small areas to increase the efficiency of growth, has resulted in extremely high concentrations of waste in localized areas which exacerbates pollution problems immensely. Combined with municipal waste from the increasing human population, the disposal of large amounts of waste products presents a significant problem. For example, in Japan about seven million tons of agricultural waste and three million tons of animal waste are discharged each year. Similarly high discharges are encountered in the USA and Europe. See, for example, "Animal Waste Pollution in America: An Emerging National Problem; Environmental Risks of Livestock & Poultry Production", Senate Committee on Agriculture, Nutrition, & Forestry (December, 1997), which discusses the health, environmental, and economic problems of animal wastes in the United States. Accordingly, there is an urgent need to address pollution problems arising from increased levels of agriculture and livestock.

Several methods to process "high strength" wastes generated by livestock and using photosynthetic organisms are known. For example, U.S. Pat. No. 3,955,318 discloses a system for treating sewage or cannery waste using unicellular algae. This system uses an algae/aerobic bacteria consortium to treat waste. However, high strength agricultural waste containing significant levels of total organic carbon (TOC) and biological oxygen demand (BOD) are not processable by this method due to the narrow culture conditions of the algae.

U.S. Pat. No. 4,267,038 discloses a system in which wastewater is treated in an anaerobic digester tank complex to reduced organic wastes, followed by treatment by an algae culture. However, the anaerobic digester treatment step is generally insufficient to remove enough contaminants from the waste stream and results in slow growth or death of the algae culture.

U.S. Pat. Nos. 4,348,285 and 4,432,869 disclose methods of treating liquid agricultural waste using (1) treatment using a combination of algae and bacteria culture, followed by (2) treatment using a rotifer culture to consume the algae/bacteria. However, most algae have a lower tolerance to raw, high strength wastes as compared to bacteria. As a result, exposure of algae to raw, high strength agricultural wastes generally results in death of the algae. Accordingly, this method is inefficient due to loss of the algae culture during use.

U.S. Pat. No. 5,795,480 discloses a method for treating wastes using heterotrophic bacteria in a first step, then treating the effluent using immobilized photosynthetic bacteria, and finally treating the effluent with photosynthetic and heterotrophic bacteria with activated sludge. However, this process does not utilize algae.

Accordingly, what is needed in the art is an efficient and cost-effective method of processing agricultural and livestock wastes that utilizes photosynthetic organisms and that preferably produces commercially valuable by-products. The present invention is believed to be an answer to that need.

SUMMARY OF THE INVENTION

In one aspect, the present invention is directed to a method for treating a waste stream containing organic and inorganic wastes, comprising the steps of: (a) contacting a waste stream comprising organic and inorganic wastes with a first mixture of microorganisms comprising one or more photosynthetic prokaryotic organisms under controlled process conditions and in the presence of light in at least one first reaction vessel, the first reaction vessel in fluid communication with at least one first photobioreactor, wherein a first portion of the wastes is assimilated by the first mixture of microorganisms to produce a partially purified waste stream comprising the first mixture of microorganisms and a second portion of the wastes; (b) removing the first mixture of microorganisms from the partially purified waste stream to produce an isolated first mixture of microorganisms and a partially purified effluent stream containing the second portion of the organic waste; (c) transferring the partially purified effluent stream from the at least one first reaction vessel to at least one second reaction vessel; (d) contacting the partially purified effluent stream with a second mixture of microorganisms comprising algae under controlled process conditions and in the presence of light in the at least one second reaction vessel, the second reaction vessel in fluid communication with at least one second photobioreactor, wherein substantially all of the second portion of the organic wastes are assimilated by the second mixture of microorganisms to produce a substantially purified waste stream comprising the second mixture of microorganisms and a substantially purified effluent; and (e) removing the second mixture of microorganisms from the substantially purified waste stream to produce an isolated second mixture of microorganisms and a substantially purified effluent stream.

In yet another aspect, the present invention is directed to a method for treating a waste stream containing organic and inorganic wastes, comprising the steps of: (a) contacting a waste stream comprising organic and inorganic wastes with a first mixture of microorganisms comprising one or more photosynthetic prokaryotic organisms under controlled process conditions and in the presence of light in at least one first photobioreactor, wherein a first portion of the wastes is assimilated by the first mixture of microorganisms to produce a partially purified waste stream comprising the first mixture of microorganisms and a second portion of the wastes; (b) removing the first mixture of microorganisms from the partially purified waste stream to produce an isolated first mixture of microorganisms and a partially purified effluent stream containing the second portion of the organic waste; (c) transferring the partially purified effluent stream from the at least one first photobioreactor to at least one second photobioreactor; (d) contacting the partially purified effluent stream with a second mixture of microorganisms comprising algae under controlled process conditions and in the presence of light in the at least one second photobioreactor, wherein substantially all of the second portion of the organic wastes are assimilated by the second mixture of microorganisms to produce a substantially purified waste stream comprising the second mixture of microorganisms and a substantially purified effluent; and (e) removing the second mixture of microorganisms from the substantially purified waste stream to produce an isolated second mixture of microorganisms and a substantially purified effluent stream.

The photobioreactor utilized in the process of the present invention preferably comprises an upstanding upwardly open structure such as a tank, a substantially transparent tube wound helically on the core structure or tubes in parallel extending from a manifold, wherein the exterior and interior of the tube or tubes are exposed to light; and means to encourage light penetration into the tube in the region of contact between the tube and the core structure. Under certain conditions in which the level of natural, ambient light is low, (e.g., high latitudes or during winter months), addition of a photobioreactor to the present invention can increase the amount of light made available to the photosynthetic microorganisms, and result in improved uptake of waste materials from the waste stream.

These and other aspects will become apparent upon reading the following detailed description of the invention.

DESCRIPTION OF THE DRAWINGS

The file of this patent contains at least one drawing executed in color. Copies of this patent with color drawing (s) will be provided by the Patent and Trademark Office upon request and payment of the necessary fee.

The invention will be more fully understood from the following detailed description taken in conjunction with the accompanying drawings, in which.

DETAILED DESCRIPTION OF THE INVENTION

Figure 1:
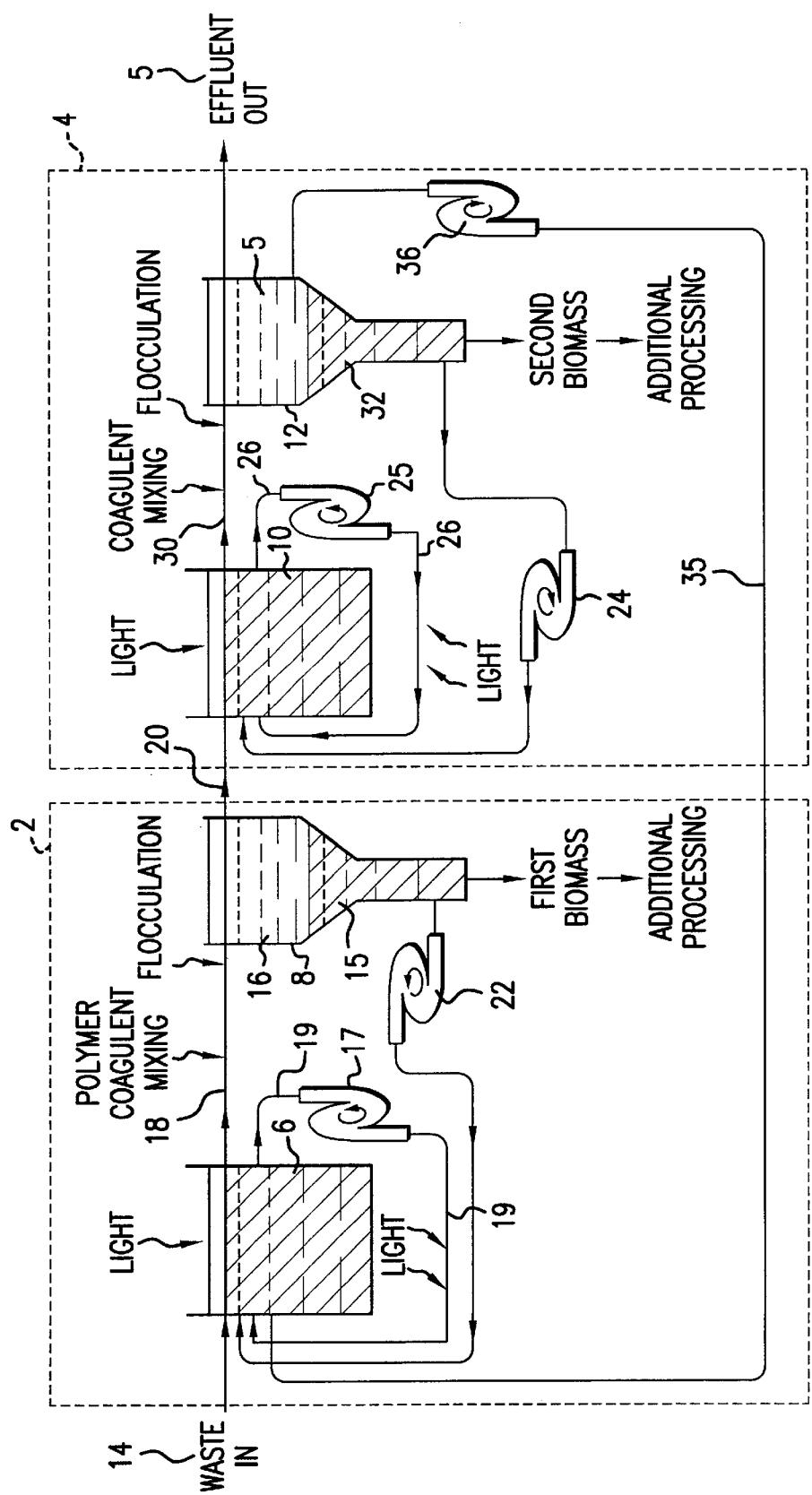
FIG. 1 is a schematic diagram of the method of the invention.

It now has been surprisingly found, in accordance with the method of the present invention, that a solution is provided to the problem of efficiently processing waste streams containing high concentrations of total organic carbon (TOC), biochemical oxygen demand (BOD), nitrogen (N) including ammonia $NH_3$, phosphorus (P, including phosphate, polyphosphates, organic phosphates, and the like), and other organic and inorganic materials. The present inventors have solved this problem by developing a multistage treatment and purification system that utilizes (1) photosynthetic prokaryotic organisms followed by (2) algae under conditions that maximize assimilation of organic and inorganic materials in the waste stream, while simultaneously maximizing water quality. The organic and inorganic materials in the waste stream are utilized as nutrient sources for the organisms, and uptake of the organic and inorganic materials in the presence of light results in growth of the organisms. A major advantage of the present invention is that the grown organisms possess high levels of crude protein, crude fat, and amino acids, and therefore are valuable as commercial agricultural products. The grown organisms can be harvested, processed, and used as animal feed supplements, fertilizers, fuels, or other useful organic products, while the purified water effluent can be used for crop irrigation or other uses. Since the products of the method of the invention are useful commercially, they do not have to be incinerated or composted thereby saving disposal costs incurred with standard waste treatment sludge generated by many conventional waste treatment processes.

Additionally, the process of the present invention differs from traditional waste treatment systems in that traditional systems are designed to maximize water quality and minimize sludge production. The process of the present invention maximizes water quality and, since the biomass is a valuable resource, maximizes biomass growth. Advantageously, this results in the ability to eliminate large concentrations of waste while generating an even higher percentage of nutritional biomass "crops". Accordingly, the present invention provides an efficient method to eliminate waste products from agricultural sources, while simultaneously producing commercially valuable organic products.

The invention utilizes strains of algae and consortia of purple non-sulfur bacteria that occur naturally, but are not typically indigenous to the raw animal waste streams. The method of the invention facilitates conditions that induce a high growth rate for these organisms and sustains this level on a continuous basis. These conditions enable the algae and bacteria to effectively treat waste streams that are over 100 times more concentrated than typical municipal waste streams that are processed by conventional municipal waste treatment systems.

The method of the present invention is very effective in removing organic and inorganic contaminants from agricultural, livestock, or municipal wastes. As described in more detail below, removal (capture) efficiencies for common water pollutants (e.g., five day biochemical oxygen demand ($BOD_5$), TOC, ammonia-nitrogen ($NH_3$—N), total phosphorous (including phosphate, polyphosphates, organic phosphates, acid-digestible phosphorous, and the like), and total suspended solids) of greater than 98 percent can be achieved using the method of the invention, with the additional benefit of producing commercially valuable by-products. This advantage makes the method of the present invention very useful, particularly on a large scale application (e.g., hog farm, cattle farm, poultry farm, etc.).

As defined herein, "photosynthetic prokaryotic organisms" refers to unicellular organisms that lack cytoplasmic inclusions (e.g., nuclear membrane, Golgi, mitochondria, endoplasmic reticulum, and the like) and that utilize light to generate at least part of the energy needed for survival. Examples of photosynthetic prokaryotic organisms include, but are not limited to, photosynthetic and/or facultative bacteria (e.g., purple non-sulfur bacteria) and cyanobacteria (blue-green algae). The term "algae" is defined herein to include green algae, euglenophytes, heterokontophytes, red algae, and cyanobacteria (blue-green algae). The term "assimilated" refers to uptake and biological transformation of organic and/or inorganic materials by an organism. The term "biomass" refers to a mass that is produced, for example, a mass of photosynthetic bacteria or algae. The term "partially purified waste stream" is defined as a waste stream that includes approximately 200–500 mg/L total organic carbon (TOC), 200–500 mg/L biological oxygen demand (BOD), 50–500 mg/L, ammonia-nitrogen ($NH_3$—N) and 10–100 mg/L total phosphorous. The term "substantially purified effluent" is defined as a waste stream that includes approximately 10–85 mg/L TOC, 5–50 mg/L BOD, 10–50 mg/L $NH_3$—N, and 10–50 mg/L total phosphorous. As defined herein, "photobioreactor" refers to a high throughput device that exposes a mixture of one or more microorganisms to varying and predefined amounts of light so that the microorganisms are optimized to generate large amounts of biomass while simultaneously removing organic and/or inorganic wastes from a waste stream. The term "reaction vessel" refers to any vessel such as a tank, pond, or other container which can be made to function as a photobioreactor within the process conditions described herein. Accordingly, it will be appreciated by those skilled in the art that the term "reaction vessel" as defined herein includes photobioreactors as described above.

FIG. 1 shows a schematic diagram of the invention. As shown in FIG. 1, the invention consists broadly of two treatment stages 2 and 4. The first treatment stage 2 generally comprises a first stage growth reactor tank 6 containing a suspension of microorganisms, preferably one or more photosynthetic and/or faculative bacteria (e.g., purple non-sulfur bacteria), and a first stage sedimentation tank 8. The second treatment stage 4 generally comprises a second stage growth reactor tank 10 containing a second suspension of microorganisms, preferably photosynthetic green algae, and a second stage sedimentation tank 12.

According to the method of the invention, wastes 14 are fed into the first stage growth reactor tank 6, and are processed through the two treatment stages 2 and 4, to produce a substantially purified effluent 5. As the wastes are processed, the suspensions of microorganisms assimilate organic and inorganic components of the waste as nutrients for growth. The organisms produced are then isolated for use as valuable commercial feed, fertilizer, and the like, as described in more detail below.

Referring now to the first treatment stage 2 in more detail, a waste stream 14 consisting of raw and untreated waste material is continuously or sequentially fed into the first stage growth reactor tank 6 by pumps, gravity, or other conventional means. It will be appreciated that more than one first stage growth reactor tank may be utilized in the method of the invention, and that the growth reactor tank may suitably be a tank, open pool, pond, or other vessel. A cover may be included with the growth reactor tank to prevent evaporation and/or contamination of the tank contents. The raw waste material may be from any source, and preferably contains organic and inorganic materials including, but not limited to, high concentrations of total organic carbon (TOC), biochemical oxygen demand (BOD), ammonia-nitrogen ($NH_3$—N) and total phosphorus (P). Preferably, the raw organic and inorganic wastes in the waste stream 14 contain from 2,000 to 80,000 mg/L BOD, 1,000 to 40,000 mg/L TOC, 200–6,000 mg/L $NH_3$—N, and 20–1,200 mg/L total phosphorous. Sources for the waste stream 14 include agricultural sources, livestock (e.g., swine, poultry, cattle, horses, sheep, and the like), food processing waste, municipal waste, beverage waste, slaughterhouse renderings, and the like. Particularly preferred sources of raw waste are livestock sources including poultry, cattle, swine, and combinations thereof. The treatment capacity of the waste stream 14 in method of the invention is generally unlimited, however typical capacity ranges from 5,000 gallons of waste per day to greater than 1 million gallons of waste per day.

As described above, the first stage growth reactor tank 6 contains a suspension of one or more microorganisms in an anoxic and/or anaerobic environment. Preferably, these photosynthetic prokaryotic organisms are a consortium of purple non-sulfur photosynthetic bacteria. According to the method of the invention, purple non-sulfur photosynthetic bacteria useful in the first treatment stage 2 include bacteria from genera Rhodospirillum, Rhodopseudomonas, Rhodobacter, Chromatium, Thiocapsia, and Rubrivivax. Particularly useful purple non-sulfur bacteria include, but are not limited to, *Rhodospirillum fulvum, Rhodospirillum rubrum, Rhodopseudomonas palustris, Rhodobacter sphaeroides, Chromatium vinosum,* and *Rubrivivax gelatinosus*. Additional nonphotosynthetic anaerobic bacteria may also be included in the mixture. According to the method of the invention, the purple non-sulfur photosynthetic bacteria may be used individually, or in suitable combinations of two, three, four, or more.

Prior to implementation of the method of the invention, the first stage growth reactor tank 6 is inoculated with a predetermined amount of the first mixture of microorganisms as a "starter" culture. The quantity of starter culture used is a function of the intended steady state mixed liquor suspended solids (MLSS) concentration in the reactors, the size of the reactors and the maximum food-to-microorganism ratio (F/M) that can be assimilated by the reactors. Generally, the starter culture may be obtained from a lyophilized stock, or from another growth reactor tank using the same organisms and conditions.

Preferably, the starter culture has been "acclimatized" to the wastes to be expected in the first stage growth reactor tank 6. Generally, this process entails exposing a selected consortium of microorganisms (e.g., equal amounts of each type of organism) to a dilute waste stream that mimics the components of the waste stream to be purified. As the concentration of waste in the dilute stream is slowly increased, the microorganisms become accustomed to assimilating the higher levels of waste, and eventually become useful for assimilating the high levels of waste in a large-scale processing plant. Alternatively, it is possible to use a starter culture that has been acclimatized to a particular waste stream (e.g., 95% hog waste and 5% poultry waste) and acclimatize it to a different waste stream (e.g., 50% hog waste and 50% poultry waste) by slowly exposing the starter culture to the new waste stream. Generally, the acclimatization process takes from several days to several months, depending on the particular waste stream to be processed.

Following inoculation, the cells proliferate and generate a large biomass that is capable of assimilating substantially all of the organic and inorganic materials in the waste stream as described in more detail below.

According to the method of the invention, the waste stream 14 flows into the first stage growth reactor tank 6 where the organic and inorganic materials in the waste are to be assimilated by the first mixture of microorganisms. Light, generally in the form of natural sunlight or suitable artificial light, is irradiated onto the mixture in order to promote assimilation of the wastes by the photosynthetic prokaryotic organisms, and to promote growth of the organisms. If artificial light is used, it is generally preferable to utilize a broad spectrum of light that is similar to sunlight, for example, fluorescent lights such as CORALIFE 50/50 Actinic/Daylight type, CORALIFE Trichromatic Super Daylight type, and the like, generating light in the range from 400–1000 nm. The artificial lighting is preferably controlled by a photoelectric switch or timer. Additionally, conduits used in the apparatus of the invention may be made of a clear or transparent material to enhance exposure to light.

The contents of the first stage growth reactor tank 6 are continuously mixed using a recirculating pump 17, paddle stirrer, or other mixing means known in the art. If a recirculating pump 17 is used, the return lines 19 are preferably made from a clear or transparent material so that the contents of the return line are exposed to light as described above.

The rate of recirculation, in addition to the direct exposure to light in the growth reactor tank, is preferably controlled to develop the proper light-to-dark ratio for optimum growth of the photosynthetic organisms. When utilizing clear return line 19 in the absence of a photobioreactor or other growth-promoting component (see below), during periods of daylight hours and/or exposure to artificial light, the present invention is typically operated with flow rates that maintain a light to dark ratio of approximately 1:600. During summer operations when natural light is at high intensity, this dark to light ratio is sufficient to maintain optimum growth. During low light periods the optimum light to dark ratio should be increased wherein light to dark volume may be as great as 1:1 or higher. As will be apparent to those skilled in the art, the conditions sufficient to achieve optimum growth will vary depending upon location, climate, and other environmental factors, such as the diurnal cycle, light intensity and time of exposure to light. Accordingly, adjustments may be required take such factors into account.

The tank contents are preferably mixed gently to avoid lysing or otherwise killing the proliferating cells. Continuous mixing of the components in the first stage growth reactor tank 6 serves several important functions, including promoting uniform contact between all the proliferating cells, soluble and colloidal waste constituents, and light, and maintaining a uniform temperature throughout the mixture. Useful temperatures of the first stage growth reactor tank 6 should generally be maintained in the range of from 28 to 40° C. In certain climates, ambient air temperature is sufficient to maintain the temperature within this range. Alternatively, the temperature of the first stage growth reactor tank 6 may be controlled using conventional heating apparatus, such as fossil fuel or solar heaters with suitable recirculating heat exchangers and associated controls. In all applications of the invention, however, the processing conditions are preferably closely controlled (e.g., temperature maintained within ±2° C.).

During the assimilation process that occurs in the first stage growth reactor tank 6, a majority of the soluble and colloidal TOC, BOD, ammonia-nitrogen, total phosphorous, and other organic and inorganic compounds associated with the waste stream 14 are utilized as nutrient sources by the first photosynthetic prokaryotic organisms. Assimilation of these waste products results in a high growth rate of the organisms, and results in the production of a large cell mass of microorganisms suspended in a partially purified liquid effluent. The growth rate of the cell mass is preferably at the exponential level, and more preferably at about 90% of the exponential level. In one embodiment, the doubling time of the cell mass ranges from about 5 days to one day.

As the large cell mass continues to grow, the contents of the first stage growth reactor tank 6 (consisting primarily of the photosynthetic prokaryotic organisms (e.g., purple non-sulfur bacteria) and partially purified liquid effluent) overflows and is transferred by a conduit 18 to a first stage sedimentation tank 8. A coagulant is added into the conduit 18 and mixed with the overflowing material in order to promote flocculation of the photosynthetic prokaryotic organisms as the material flows into the first stage sedimentation tank 8. Alternatively, the material overflowing from the first stage growth reactor tank 6 may be collected in a first stage coagulation tank (not shown), mixed with coagulant, and gently agitated to agglomerate the cells.

In accordance with the method of the invention, useful coagulants include high molecular weight cationic polymers, such as MAGNIFLOC 496C, MAGNIFLOC 234GD (available commercially from Cytec Industries), and the like. Preferably, the coagulants used in the invention meet the USFDA standard of GRAS (Generally Regarded As Safe). During processing of the waste stream, coagulant is generally added in amounts that effectively agglomerate the photosynthetic prokaryotic organisms. Typical amounts of added coagulant preferably range from 0 to 2% dry weight of polymer, and more preferably from 0 to 1.2% dry weight of polymer, all based on the total dry weight of the flocculated cells.

Figure 2:
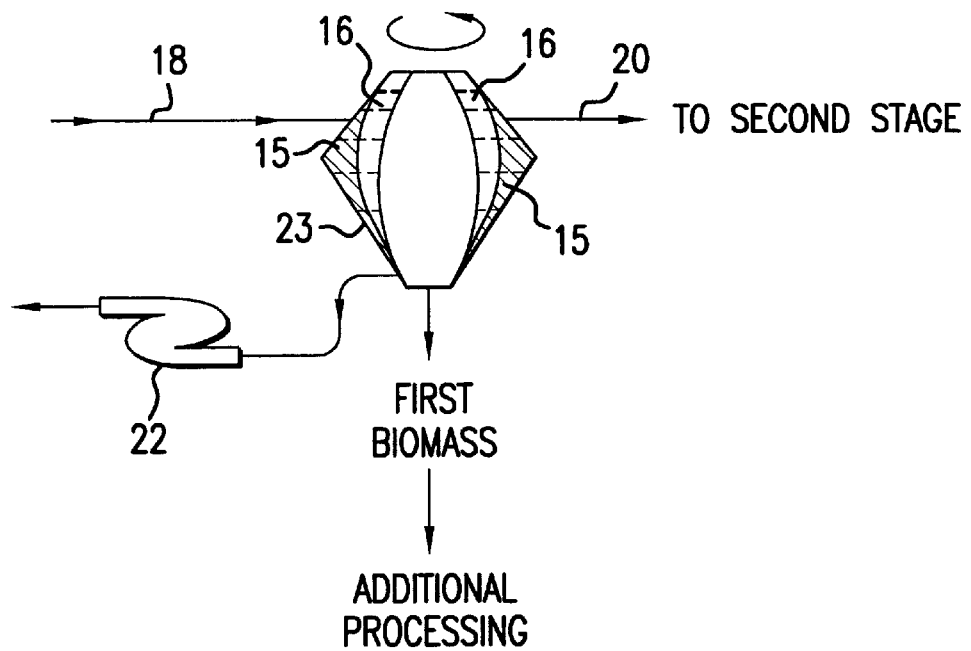
FIG. 2 is a schematic diagram of an alternative embodiment of the invention.

The mixture of flocculated microorganisms, liquid effluent, and coagulant are collected in the first stage sedimentation tank 8 where the flocculated cells are physically separated from the liquid effluent. Generally, the separation process occurs by gravity sedimentation and/or flotation after a sufficient amount of time, generally 2 to 12 hours. Alternatively, more rapid separations of the microorganisms and effluent may be achieved by replacing the first stage sedimentation tank 8 with a continuous centrifuge 23 (shown in FIG. 2), or other rapid separation method known in the art. If a continuous centrifuge is employed, general operating parameters according to the method of the invention include a spin speed of 3,000–4,000 RPM, centrifugal force of approximately 3,000–4,000×g, and a spin time of between about 1–5 minutes.

A return system for the mixture of microorganisms is incorporated into the first treatment stage 2. This system consists of a pump 22 that transports the microorganisms from the first stage sedimentation tank 8 (or centrifuge 23) back to the first stage growth reactor tank 6. This system is utilized in the event the optimum hydraulic retention time (HRT) is significantly less than the optimum mean cell residence time (MCRT) in the first stage growth reactor tank 6. For example, if the optimum doubling rate of the biomass is achieved with a mean cell residence time of 4 days and the reactor can remove the applicable organic load within one day then a 25% recycle of biomass is required. Alternatively the recirculation of liquid effluent from the first stage sedimentation tank 8 (or centrifuge) may be used as a substitute for water in diluting the wastes 14 entering the first stage growth reactor 6. This recycle is desirable as it reduces the hydraulic loading on the second stage growth reactor tank 10 thereby potentially reducing the size of the second treatment stage 4 and saving on energy and coagulant. Accordingly, the recirculating system assures that the maximum amount of waste materials are assimilated by the first mixture of microorganisms in the first treatment stage 2 while minimizing the size of the overall system.

Following separation, the biomass of first microorganisms are removed from the first stage sedimentation tank 8 (or centrifuge 23), and may be further refined using processes such as dewatering, drying, pasteurization, pelletizing, and the like, depending on the intended use of the flocculated organisms. The harvested biomass of processed flocculated organisms are then available to be sold either as animal feed, fertilizer, or other agricultural product. Generally, when processed as described above, purple non-sulfur bacteria possesses from 40–60% by weight protein, 10–15% by weight fat and 1–5% by weight fiber, all based on the total dry weight of the processed organisms.

During the first treatment stage 2, the range of conditions outlined in Table 1 are preferably used and are automatically or manually controlled and optimized at all times.

TABLE 1

Preferred Conditions For First Treatment Stage

| | |
|---|---|
| Hydraulic Retention Time (HRT) | 1–10 days |
| Mixed Liquor Suspended Solids (MLSS) | 500–4000 mg/liter |
| Mean Cell Residence Time (MCRT) | 1–10 days |
| Food to Microorganism ratio (F/M), based on BOD loading | 0.3–2.0 per day |
| Food to Microorganism ratio (F/M), based on $NH_3$—N loading | 0.06–0.36 per day |
| BOD loading per unit volume of reactor | 19–77 kg per day per 28,300 liters |
| $NH_3$—N loading per unit volume of reactor | 2.4–14 kg per day per 28,300 liters |
| Dilution ratio (vol. dilution water per vol. raw waste) | 0/1 to 8/1 |
| Effluent return ratio (vol. effluent returned per vol. raw waste) | 0/1 to 8/1 |
| Biomass return ratio (from liquid solids separation unit to reactor) | 0–25% by volume |
| Temperature | 28–40° C. |
| pH | 7.0–8.5 |
| Mixing turnover | 3 min to 12 hrs. |

In Table 1, Hydraulic Retention Time (HRT) refers to the average time that liquid is in a reactor or sedimentation tank or centrifuge (computed as the reactor liquid volume divided by the flow rate through the reactor). Mixed Liquor Suspended Solids (MLSS) refers to the total suspended solids (TSS) concentration in the reactor. Mean Cell Residence Time (MCRT) refers to the average time that a microbial cell is in the reactor (computed as the total suspended solids (MLSS) in the reactor divided by the suspended solids flow through the reactor). Food-to-Microorganism Ratio (F/M) is based on either the BOD or $NH_3$—N loading in pounds per day divided by the total weight of MLSS in the reactor. DOD or $NH_3$—N loading per unit volume of reactor is based on either DOD or $NH_3$—N loading in pounds per day divided by the total liquid volume in the reactor. The Dilution Ratio refers to the dilution water flow into the reactor divided by the waste flow into the reactor. Effluent Return Ratio refers to the effluent return flow into the reactor divided by the waste flow into the reactor. Biomass Return Ratio refers to the flow rate for biomass slurry returned to the reactor from the liquid/solids separation unit divided by the influent waste flow rate to the reactor.

The mixture of microorganisms used in the second treatment stage 4 of the present invention are generally less tolerant to high levels of organic wastes. Accordingly, following treatment in the first treatment stage 2, the TOC, BOD, $NH_3$—N, and phosphorus in the liquid effluent are preferably reduced to approximately 200–500 mg/L TOC, 200–500 mg/L BOD, 50–500 mg/L, $NH_3$—N and 10–100 mg/L total phosphorous. These levels of contaminants are preferred to minimize loss of the microorganisms in the second stage of the treatment process due to cell death.

The liquid effluent 16 that remains in the first stage sedimentation tank 8 (or centrifuge 23) either flows into the second treatment stage 4 via a conduit 20 and into one or more second stage growth reactor tanks 10, and/or is recycled as dilute for the raw waste entering the first stage growth reactor tank 6. The second stage growth reactor tank 10 contains a second mixture of microorganisms that are controlled to optimize the balance between respiration and photosynthesis. Like the first stage growth reactor tank, the second stage growth reactor tank may suitably be a tank, open pool, pond or other vessel. A cover may be included with the growth reactor tank to prevent evaporation and/or contamination of the tank contents. Preferably, the second mixture of microorganisms are selected from green algae (e.g., Chlorophyta) including unicellular and filamentous species, Pyrrhophyta, Heterokontophyta, Euglenophyta, and the line of cyanobacteria (blue-green algae). Particularly useful members of Chlorophyta include species selected from the genera Chlorella (e.g., *Chlorella vulgaris, Chlorella pyrenoidosa*), Scenedesmus (e.g., *Scenedesmus obliquus, Scenedesmus quadricauda, Scenedesmus acutus*), Oocystis, and Euglena (e.g., *Euglena gracilis*). Useful members of the cyanobacteria include species selected from the genera Spirulina (e.g., *Spirulina platensis*), Oscillatoria, and Phormidium (e.g., *Phormidium bohneri*). Combinations of two, three or more of these algae may also be used. Symbiotic bacteria may also be present in the second mixture of microorganisms.

Like the first stage growth reactor tank, the second stage growth reactor tank 10 is inoculated with a predetermined amount of the second microorganisms as a "starter" culture prior to implementation of the method of the invention. Generally, the starter culture may be obtained from stock cultures, or from another growth reactor tank using the same organisms. The cultures are preferably acclimatized using the same procedures as described above.

Light, generally in the form of natural sunlight or suitable artificial light, is irradiated onto the mixture in the second stage growth reactor tank 10 in order to promote further absorption of the organic wastes by the second mixture of microorganisms, and to promote growth of the organisms. As with the first stage reactor, if artificial light is used, it is generally preferable to utilize a broad spectrum of light that is similar to sunlight, as described above.

As discussed above for the first growth reactor tank, the rate of recirculation, in addition to the direct exposure to light in the second growth reactor tank, is preferably controlled to develop the proper light-to-dark ratio for optimum growth of the photosynthetic organisms. Use of clear return line 26 in the absence of a photobioreactor or other growth-promoting component (see below), during periods of daylight hours and/or exposure to artificial light, the present invention is operated with flow rates that maintain a light to dark ratio of approximately 1:600. During summer operations when natural light is at high intensity, this dark to light ratio is typically sufficient to maintain optimum growth. During low light periods the optimum light to dark ratio should be increased wherein light to dark volume may be as great as 1:1 or higher. As will be apparent to those skilled in the art, the conditions sufficient to achieve optimum growth will vary depending upon location, climate, and other environmental factors, such as the diurnal cycle, light intensity and time of exposure to light. Accordingly, adjustments may be required take such factors into account.

The contents of the second stage growth reactor tank 10 are continuously mixed using a recirculating pump 25, paddle stirrer, or other mixing means known in the art. If a recirculating pump 25 is used, the return lines 26 are preferably made from a clear or transparent material so that the contents of the return line are exposed to light as described above.

The tank contents are preferably mixed gently to avoid lysing or otherwise killing the proliferating cells. Continuous mixing of the components in the second stage growth reactor tank 10 serves several important functions, including promoting uniform contact between all the microorganisms, soluble/colloidal waste constituents, and light, and to maintain a uniform temperature throughout the mixture. Useful temperatures for the second stage growth reactor tank 10 should generally be maintained in the range of from 20 to 35° C. In certain climates, ambient air temperature is sufficient to maintain the temperature within this range. Alternatively, the temperature of the second stage growth reactor tank 6 may be controlled using conventional heating apparatus, such as fossil fuel or solar heaters with suitable recirculating heat exchangers and associated controls.

The pH of the mixture in the second stage growth reactor tank 10 is particularly important to maintain the viability of the second mixture of microorganisms. Preferably, the pH of the contents of the second stage growth reactor tank is maintained between 7.0 and 8.5 by addition of aqueous solutions of base (e.g., sodium bicarbonate, calcium bicarbonate, sodium hydroxide, potassium hydroxide, and the like), or acids (carbon dioxide, hydrochloric acid, acetic acid, and the like).

During the assimilation process that occurs in the second stage growth reactor tank 10, substantially all of the remaining soluble and colloidal TOC, BOD, ammonia-nitrogen, total phosphorous, and other organic and inorganic compounds associated with the waste are absorbed as nutrient sources by the second mixture of microorganisms. Assimilation of these waste products results the production of a large cell mass of microorganisms suspended in a substantially purified liquid effluent.

As the large cell mass in the second stage growth reactor tank 10 continues to grow, the contents (consisting primarily of green algae and substantially purified liquid effluent) overflows and is transferred by a conduit 30 to a second stage sedimentation tank 12. A coagulant is added into the conduit 30 and mixed with the overflowing material in order to promote flocculation of the second mixture of microorganisms as the material flows into the second stage sedimentation tank 12. Alternatively, the material overflowing from the second stage growth reactor tank 10 may be collected in a second stage coagulation tank (not shown), mixed with coagulant, and gently agitated to agglomerate the cells. Exemplary coagulants amounts useful in the second stage 4 are the same as described above for the first stage 2.

Figure 3:
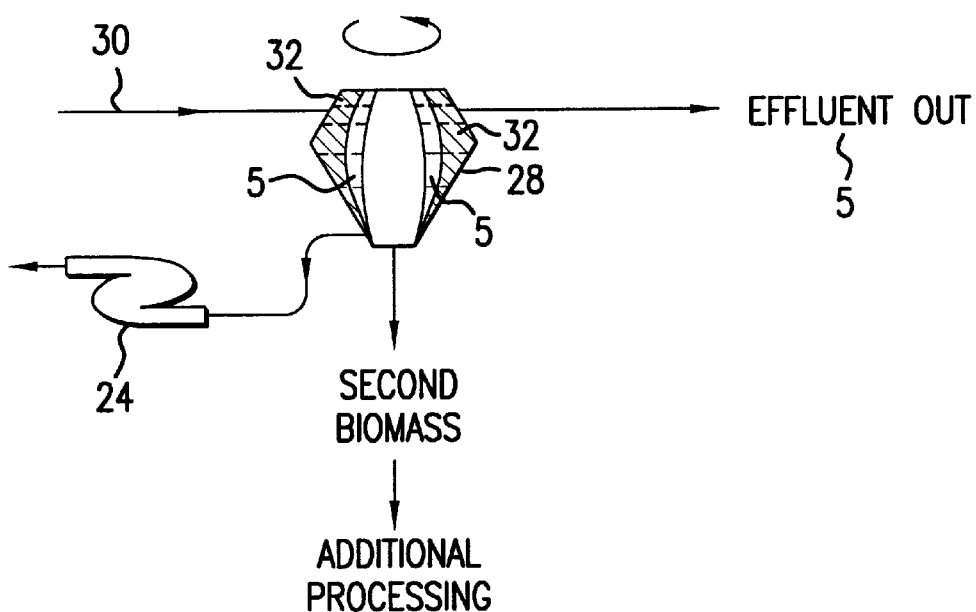
FIG. 3 is a schematic diagram of another alternative embodiment of the invention.

The mixture of flocculated organisms, liquid effluent, and coagulant are collected in the second stage sedimentation tank 12 where the flocculated cells are physically separated from the liquid effluent. Like the first stage 2, the separation process occurs by gravity sedimentation and/or flotation after a sufficient amount of time, generally 2–12 hours. Alternatively, more rapid separations of the organisms and effluent may be achieved by replacing the second stage sedimentation tank 12 with a continuous centrifuge 28 (shown in FIG. 3), a filter press, or other rapid separation method known in the art. If a continuous centrifuge is employed, general operating parameters according to the method of the invention include a spin speed of 3,000–4,000 RPM, centrifugal force of approximately 3,000–4,000×g, and a spin time of between about 1–5 minutes.

Like the first treatment stage 2, a return system for the second mixture of microorganisms is incorporated into the second treatment stage 4. This system consists of a pump 24 that transports the second mixture of microorganisms from the second stage sedimentation tank 12 back to the second stage growth reactor tank 10. This system is utilized in the event the optimum hydraulic retention time (HRT) is significantly less than the optimum mean cell residence time (MCRT) in the second stage growth reactor tank 10. Accordingly, this system assures that the maximum amount of waste materials are assimilated by the second mixture of microorganisms in the second treatment stage 4.

Following separation, the biomass of microorganisms 32 are removed from the second stage sedimentation tank 12 (or centrifuge 28), and may be further refined using processes such as dewatering, drying, pasteurization, pelletizing, and the like, depending on the intended use of the flocculated organisms. The harvested biomass of processed flocculated organisms are then available to be sold either as animal feed, fertilizer, or other agricultural product. Generally, green algae processed as described above possesses from 60–85% by weight protein, 1–5% by weight fat and 1–10% by weight fiber, all based on the total dry weight of the processed organisms. The liquid effluent 5 can be disposed of in various ways depending on site and project specific conditions and requirements. For example, the effluent 5 can be used to irrigate animal feed crops, or may be further purified using activated carbon and used to irrigate commercial crops for human consumption. Alternatively, the effluent 5 may be discharged to groundwater using infiltration basins or an underground structure. According to the method of the invention, a portion of the effluent 5 may also be recycled to the first treatment stage 2 via a conduit 35 and pump 36 for the purpose of adjusting the concentration of incoming raw waste or recycled to the second stage growth reactor tank as describe for the first treatment stage.

During the second treatment stage 4, the following range of conditions outlined in Table 2 are preferably used and are automatically or manually controlled at all times.

TABLE 2

| Preferred Conditions For Second Treatment Stage | |
| --- | --- |
| Hydraulic Retention Time (HRT) | 1–12 days |
| Mixed Liquor Suspended Solids (MLSS) | 500–4000 mg/liter |
| Mean Cell Residence Time (MCRT) | 1–12 days |
| Food to Microorganism ratio (F/M), based on BOD loading | 0.02 per day to 0.2 per day |
| Food to Microorganism ratio (F/M), based on $NH_3$—N loading | 0.01 per day to 0.1 per day |
| BOD loading per unit volume of reactor | 0.6–5 kg per day per 28,300 liters |
| $NH_3$—N loading per unit volume of reactor | 0.2–2 kg per day per 28,300 liters |
| Dilution ratio (vol. dilution water per vol. first stage effluent) | 0/1 to 4/1 |
| Effluent return ratio (vol. effluent returned per vol. first stage effluent) | 0/1 to 4/1 |
| Biomass return ratio (from liquid solids separation unit to reactor) | 0–25% by weight |
| Temperature | 20–35° C. |
| pH | 7.0–8.5 |
| Mixing turnover | 3 min to 12 hrs. |

Following the treatment in the second stage sedimentation tank 12 (or centrifuge), the TOC, BOD, $NH_3$—N, and phosphorus in the liquid effluent have been reduced to approximately 10–85 mg/L TOC, 5–50 mg/L BOD, 10–50 mg/L $NH_3$—N, and 10–50 mg/L total phosphorous.

Figure 5:
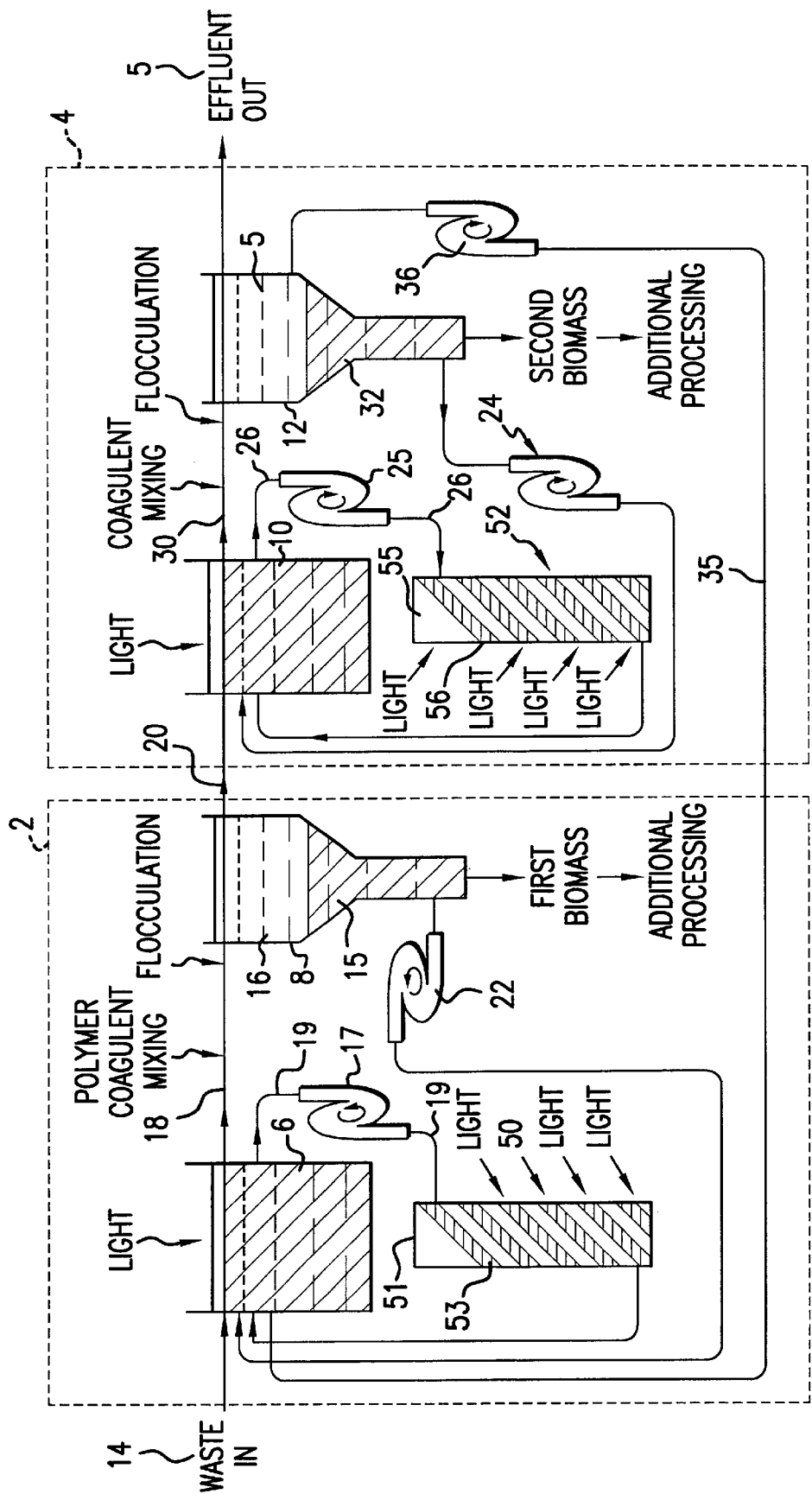
FIG. 5 a schematic diagram of an alternative embodiment of the method of the invention that includes photobioreactors.

Under certain conditions in which the level of natural, ambient light is low, (e.g., high latitudes or during winter months), addition of a supplemental photobioreactor to the present invention can increase the amount of light made available to the photosynthetic microorganisms, and result in improved uptake of waste materials from the waste stream. In order to enhance the uptake of organic and inorganic waste materials from the waste stream 14, one or more photobioreactors 50 and 52 may be installed in the return lines 19 and 25 of the present invention, respectively, as shown in FIG. 5. The photobioreactors utilized in this embodiment of the present invention include any high throughput device capable of processing a mixture of one or more microorganisms and wastes, and capable of continuously removing organic and/or inorganic materials from the wastes while simultaneously generating large amounts of biomass. The supplemental photobioreactors implemented in this embodiment of the present invention preferably provide additional light to the growing cell mass to enhance and optimize the growth rate of the organisms.

In one particularly preferred embodiment, the photobioreactors 50 and 52 preferably comprise an upstanding core structure 51, 55, a substantially transparent tube 53, 56 wound on the core structure, wherein the exterior of the wound tube is exposed to light, and means to encourage light penetration into the tube in the region of contact between the tube and the core structure. Examples of useful photobioreactors according to the method of the invention include coiled tubular photobioreactors of the type described and illustrated in U.S. Pat. No. 5,137,828, herein incorporated by reference in its entirety, and available commercially under the tradename "BIOCOIL" and are available from Biotechna Environmental International, LTD.

Briefly, "BIOCOIL"-type photobioreactors comprise an upstanding core structure, and a substantially transparent tube wound on the core structure, or tubes wound in parallel on a manifold such that the exterior of the tubes are exposed to light. The upstanding core structure preferably includes a reflective coating, such as white paint, aluminum foil, small glass balls, and the like, interposed between the core structure and the transparent tubing. This reflective coating enhances light penetration into the transparent tubing in the region where the transparent tubing and the core structure make contact and thereby increases the amount of available light.

As light passes through the materials in the growth reactor tanks, a portion of the light is absorbed and utilized for growth of the microorganisms. However, the light intensity is lowest at the bottom of the growth reactor tanks 6 and 10. Supplemental photobioreactors utilized in this alternative embodiment of the present invention aid in the uptake of organic and inorganic wastes by the microorganisms at the bottom of the growth reactor tanks 6 and 10 by providing additional light exposure to the photosynthetic microorganisms at the bottom of the first and second growth reactor tanks 6 and 10. Materials in the growth reactor tanks are taken from the bottom of each tank and processed through the respective photobioreactors. During this processing, the photosynthetic microorganisms are exposed to a high number of photons per unit volume, and results in increased uptake of waste materials. Addition of the photobioreactors therefore results in an increased overall efficiency of the process of the invention and can provide additional light to the organisms during times at which ambient light levels are low (e.g., winter months).

Additional photobioreactors that may be used according to the process of the present invention are described in British Patent Application No. 9719965.7, and in U.S. Pat. Nos. 4,868,123; 4,952,511; 5,162,051; and 5,447,629.

Figure 6:
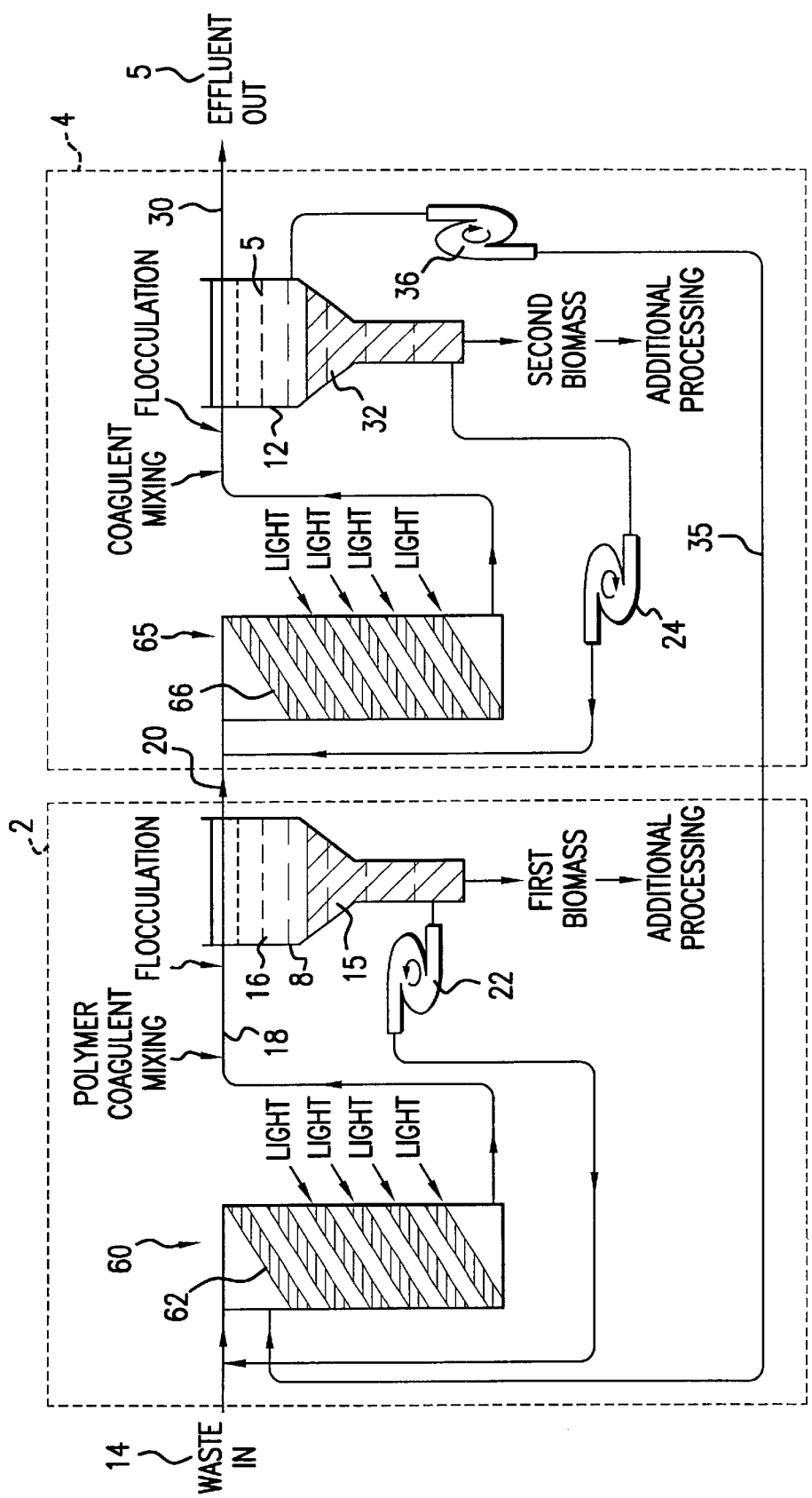
FIG. 6 a schematic diagram of another alternative embodiment of the method of the invention that includes higher light efficiency photobioreactors.

In another alternative embodiment shown in FIG. 6, the first stage growth reactor tank 6 and the second stage growth reactor tank 10 are replaced with any type of photobioreactors which provide for higher light transfer, each comprising an upstanding core structure and a substantially transparent tube wound on the core structure, or a tube wound in parallel on a manifold such that the exterior of the wound tubes are exposed to light as described above.

In this alternative embodiment, a waste stream 14 consisting of raw and untreated waste material is continuously or sequentially fed into the first photobioreactor 60 by pumps, gravity, or other conventional means. It will be appreciated that more than one first photobioreactor may be utilized in the method of the invention. The raw waste material may be from any source, as described above.

The first photobioreactor 60 contains a suspension of one or more microorganisms in an anoxic and/or anaerobic environment. Preferably, these photosynthetic prokaryotic organisms are a consortium of purple non-sulfur photosynthetic bacteria as described above. Additional nonphotosynthetic anaerobic bacteria may also be included in the mixture.

Prior to implementation of the method of the invention, the first photobioreactor 60 is inoculated with a predetermined amount of the first mixture of microorganisms as a "starter" culture. The quantity of starter culture used is a function of the intended steady state mixed liquor suspended solids (MLSS) concentration in the reactors, the size of the reactors and the maximum food-to-microorganism ratio (F/M) that can be assimilated by the reactors. Generally, the starter culture may be obtained from a lyophilized stock, or from another growth reactor tank using the same organisms and conditions. Preferably, the starter culture has been "acclimatized" as described earlier.

Following inoculation, the cells proliferate and generate a large biomass that is capable of assimilating substantially all of the organic and inorganic materials in the waste stream as described in more detail below.

According to the method of the invention, the waste stream 14 flows into the first photobioreactor 60 where the organic and inorganic materials in the waste are to be assimilated by the first mixture of microorganisms. Light, generally in the form of natural sunlight or suitable artificial light, is irradiated onto the transparent coils 62 of the photobioreactor 60 in order to promote assimilation of the wastes by the photosynthetic prokaryotic organisms, and to promote growth of the organisms.

The contents of the first photobioreactor 60 are mixed gently by turbulence in the transparent tubing 62 to avoid lysing or otherwise killing the proliferating cells. Continuous mixing of the components in the first stage growth reactor tank 6 serves several important functions, including promoting uniform contact between all the proliferating cells, soluble and colloidal waste constituents, and light, and maintaining a uniform temperature throughout the mixture. Useful temperatures in the first photobioreactor 60 should generally be maintained in the range of from 25 to 40° C. In certain climates, ambient air temperature is sufficient to maintain the temperature within this range. Alternatively, the temperature of the first photobioreactor 60 may be controlled using conventional heating apparatus, such as fossil fuel or solar heaters with suitable recirculating heat exchangers and associated controls. In all applications of the invention, however, the processing conditions are preferably closely controlled (e.g., temperature maintained within ±2° C.).

During the assimilation process that occurs in the first photobioreactor 60, a majority of the soluble and colloidal TOC, BOD, ammonia-nitrogen, total phosphorous, and other organic and inorganic compounds associated with the waste stream 14 are utilized as nutrient sources by the first photosynthetic prokaryotic organisms as described for the growth reactor tanks. Assimilation of these waste products results in a high growth rate of the organisms, and results in the production of a large cell mass of microorganisms suspended in a partially purified liquid effluent. The growth rate of the cell mass is preferably at the exponential level, and more preferably at about 90% of the exponential level.

As the cell mass continues to grow, the contents of the photobioreactor 60 (consisting primarily of the photosynthetic prokaryotic organisms (e.g., purple non-sulfur bacteria) and partially purified liquid effluent) traverses the clear tubing 62 and is transferred by a conduit 18 to the first stage sedimentation tank 8 (or centrifuge 23). The remaining steps of the process, including addition of coagulant, sedimentation or centrifugation, return system, and additional processing of the harvested biomass, are conducted as described above for the first growth reactor tank and first sedimentation tank.

Referring again to FIG. 6, the liquid effluent that remains in the first stage sedimentation tank 8 (or centrifuge 23) flows into the second treatment stage 4 via a conduit 20 and into one or more second photobioreactors 65. As described above for the second growth reactor tank, the second photobioreactor 65 contains a second mixture of microorganisms that are controlled to optimize the balance between respiration and photosynthesis. Preferably, these organisms are selected from green algae (e.g., Chlorophyta) including unicellular and filamentous species, Pyrrhophyta, Heterokontophyta, Euglenophyta, and the line of cyanobacteria (blue-green algae) as described above.

Like the first photobioreactor, the second photobioreactor 65 is inoculated with a predetermined amount of the second microorganisms as a "starter" culture prior to implementation of the method of the invention. Light, generally in the form of natural sunlight or suitable artificial light, is irradiated onto the mixture in the photobioreactor 65 in order to promote further absorption of the organic wastes by the second mixture of microorganisms, and to promote growth of the organisms. As with the first photobioreactor, if artificial light is used, it is generally preferable to utilize a broad spectrum of light that is similar to sunlight, as described above.

The contents of the second photobioreactor 65 are continuously mixed by the turbulence in the transparent tubing 66 to avoid lysing or otherwise killing the proliferating cells. Like the first photobioreactor, useful temperatures for the second stage growth reactor tank 10 should generally be maintained in the range of from 20 to 35° C. In certain climates, ambient air temperature may be sufficient to maintain the temperature within this range. Alternatively, a conventional heating apparatus may be used as described above.

The pH of the mixture in the second photobioreactor 65 is preferably maintained between 7.0 and 8.5 by addition of aqueous solutions of base (e.g., sodium bicarbonate, sodium hydroxide, potassium hydroxide, and the like), or acids (carbon dioxide, hydrochloric acid, aqueous acetic acid, and the like) as described above. Preferably, the volumetric flow through the photobioreactors shown in FIGS. 5 and 6 is such that the ratio of material that is not exposed to light to the material that is exposed to light (D:L ratio) ranges from 600:1 to 1:1, is more preferably in the range of 100:1 to 1:1, and most preferably in the range of 50:1 to 1:1. Generally, those of skill in the art can easily determine the proper ratio of dark to light required to provide optimum uptake of waste materials and maximum generation of biomass at a given level of ambient light.

During the assimilation process that occurs in the second photobioreactor, substantially all of the remaining soluble and colloidal TOC, BOD, ammonia-nitrogen, total phosphorous, and other organic and inorganic compounds associated with the waste are absorbed as nutrient sources by the second mixture of microorganisms. Assimilation of these waste products results the production of a large cell mass of microorganisms suspended in a substantially purified liquid effluent.

As the large cell mass in the second photobioreactor 65 continues to grow, the contents (consisting primarily of green algae and substantially purified liquid effluent) traverses the clear tubing 66 and is transferred by a conduit 30 to the second stage sedimentation tank 12 (or centrifuge 23). The remaining steps of the process, including addition of coagulant, sedimentation or centrifugation, return system, processing of the harvested biomass and effluent, are conducted as described above for the second growth reactor tank and first sedimentation tank.

The following Examples are intended to illustrate, but in no way limit the scope of the present invention. All parts and percentages are by weight and all temperatures are in degrees Celsius unless explicitly stated otherwise.

EXAMPLES

Example 1

Laboratory Scale Photosynthetic Purification Process

The swine waste used in this example was a thick gray liquid slurry, with a pungent, offensive odor. The waste components included feces, urine, and washwater.

A consortium of purple non-sulfur bacteria were used as the first mixture of microorganisms, and consisted mainly of *Rhodospirillum fulvum, Rhodospirillum rubrum, Rhodopseudomonas palustris, Rhodobacter sphaeroides, Chromatium vinosum,* and *Rubrivivax gelatinosus*. Initial cultures were grown from one liter sample as described above for a starter culture. These organisms were in the form of a red/brown liquid with a strong odor.

The second mixture of microorganisms consisted mainly of the green algae strain Chlorella. Initial cultures were grown from one liter sample as described above for a starter culture. The material was a dark green liquid, which lacked a strong odor.

The first and second stage growth reactor tanks were made of plastic (18.5 inches H×6 inches W×4 inches D) and were arranged as described above. The first stage growth reactor tank contained 5.5 liters of the consortium of purple non-sulfur bacteria. The second stage growth reactor tank was a combination of two tanks connected in parallel and holding a total of 11 liters of Chlorella algae culture. The two second stage growth reactor tanks were mixed so as to simulate one completely mixed tank.

The first stage growth reactor tank was supplied with light from two fluorescent fixtures. The bulbs used in the Red tank were "Coralife 50/50 Actinic/Daylight" type. The second stage growth reactor tanks were supplied with light by five fluorescent fixtures. The bulbs used in these tanks were "Coralife Trichomatic Super Daylight" type. Dark-to-light (D/L) ratio for both reactors is 1.0, i.e., 12 hours "on" and 12 hours "off". Each tank was heated to 32° C. using immersion type heaters, and each tank was stirred using a laboratory stirring apparatus. Additionally mixing between the two second stage growth reactor tanks was facilitated by a peristaltic pump. Additionally, the pH was held between 7.2 and 7.8 using controlled addition of hydrochloric acid (HCl) or acetic acid ($CH_3COOH$). A 0.2% solution of "MAGNIFLOC" 496C cationic polymer was used to flocculate samples of each of the cellular cultures.

The consortium of purple non-sulfur bacteria was fed daily with approximately 200 ml of swine waste diluted to approximately 5.5 liters with water. This feeding regimen resulted in a Mean Cell Residence Time (MCRT) and Hydraulic Retention Time (HRT) of 5.5 days for the first stage. One liter of this culture was removed daily, and 10–20 ml of cationic polymer is added with stirring to flocculate the cells. The flocculated cellular slurry was filtered using a Buchner funnel and a 9 micron filter paper (Whatman No. 40). The liquid portion (filtrate) was analyzed for waste content (see Table 3 below) and utilized as feedstock for the Chlorella in the second growth reactor tank.

Equal volumes of the filtrate from the first stage growth reactor tank were used to feed the Chlorella culture in the two second growth reactor tanks. This feeding regimen produces a Mean Cell Residence Time (MCRT) and Hydraulic Retention Time (HRT) of 11 days in the second stage growth reactor tanks.

One liter of Chlorella culture was removed daily from the second growth reactor tanks. 10–20 ml of cationic polymer was added to precipitate the Chlorella cells, and the flocculated slurry was filtered using a Buchner funnel and 9 micron filter paper. A sample of the liquid portion (filtrate) was analyzed for TOC, BOD, nitrogen, and total phosphorous content as shown in Table 3.

TABLE 3

Capture Efficiencies for Laboratory Scale Photosynthetic Swine Waste Treatment

|  | Raw Waste (g/l) | 1st Stage Effluent (mg/l) | 2nd Stage Effluent (mg/l) | 1st Stage Removal Eff. (%) | 2nd Stage Removal Eff. (%) | Overall Removal Eff. (%) |
|---|---|---|---|---|---|---|
| TOC | 10,000 | 250 | 40 | 97.5 | 84.0 | 99.6 |
| BOD | 25,000 | ND* | 6 |  |  | 99.9 |
| $NH_3$—N | 3,200 | 300 | 40 | 90.6 | 86.6 | 98.7 |
| Total P-P | 600 | 80 | 40 | 86.6 | 50.0 | 93.3 |

*Not Determined

The amounts of useable protein in the isolated purple non-sulfur bacterial consortium and the isolated Chlorella are shown in Table 4. Nutritional amounts of protein available in each biomass are deduced by subtracting the "protein equivalent" from the total protein percentage.

TABLE 4

Nutritional Amounts Of Protein Available In Biomasses

|  | Total Protein (% wet) | Protein Equivalent (% wet) | Nutritional Protein (% wet) | % Moisture | Nutritional Protein (% Dry) |
|---|---|---|---|---|---|
| Purple Non-Sulfur Bacterial Consortium | 5.32 | 0.8 | 4.52 | 81.6 | 24.56 |
| Green algae (Chlorella) | 55.2 | 4.25 | 50.95 | 0.07 | 59.35 |

Example 2

Pilot Scale Photosynthetic Purification Process

The swine waste used in this Example was a thick gray liquid slurry, with a pungent, offensive odor. The waste components are feces, urine, and washwater. In this Example, raw waste from the collection sump of a hog farm in Connecticut is fed into the system on a continuous, batch, or semicontinuous batch basis. The higher efficiencies associated with continuous recirculation, natural light and other factors diminished the strong odor emanating from the biomass in the 1st stage reactor. The reactor was capable of processing 4 gallons per day of raw hog waste.

A consortium of purple non-sulfur bacteria harvested from the laboratory scale reactor in Example 1 were used as the first mixture of microorganisms, and consisted mainly of *Rhodospirillum fulvum, Rhodospirillum rubrum, Rhodopseudomonas palustris, Rhodobacter sphaeroides, Chromatium vinosum,* and *Rubrivivax gelatinosus.* These organisms are in the form of a red/brown liquid with a strong odor.

The second mixture of microorganisms consisted mainly of the green algae strain Chlorella which were harvested from the laboratory scale reactor in Example 1. The Chlorella material was a dark green liquid, which lacks a strong odor. Again, the higher efficiencies associated with continuous recirculation, natural light, and other factors enhanced the performance of the biomass in the second stage reactor.

The first and second stage growth reactor tanks, sedimentation and flocculation tanks were made of plastic, and the pilot plant has an overall volume of approximately 240 gallons. Samples were processed as described in Example 1. Samples of the liquid portion (filtrate) were analyzed for TOC, BOD, nitrogen, and total phosphorous content as shown in Table 5.

TABLE 5

Capture Efficiencies for Pilot Scale Photosynthetic Swine Waste Treatment

|  | Raw Waste (g/l) | 1st Stage Effluent (mg/l) | 2nd Stage Effluent (mg/l) | 1st Stage Removal Eff. (%) | 2nd Stage Removal Eff. (%) | Overall Removal Eff. (%) |
|---|---|---|---|---|---|---|
| TOC | 9,400 | 650 | 85 | 93.0 | 86.9 | 99.0 |
| BOD | 19,000 | 450 | 25 | 97.6 | 94.4 | 99.8 |
| $NH_3$—N | 1,980 | 138 | 15.8 | 93.0 | 88.5 | 99.2 |
| Total P-P | 212 | 66.3 | 16.2 | 68.7 | 75.5 | 92.3 |

Figure 4:
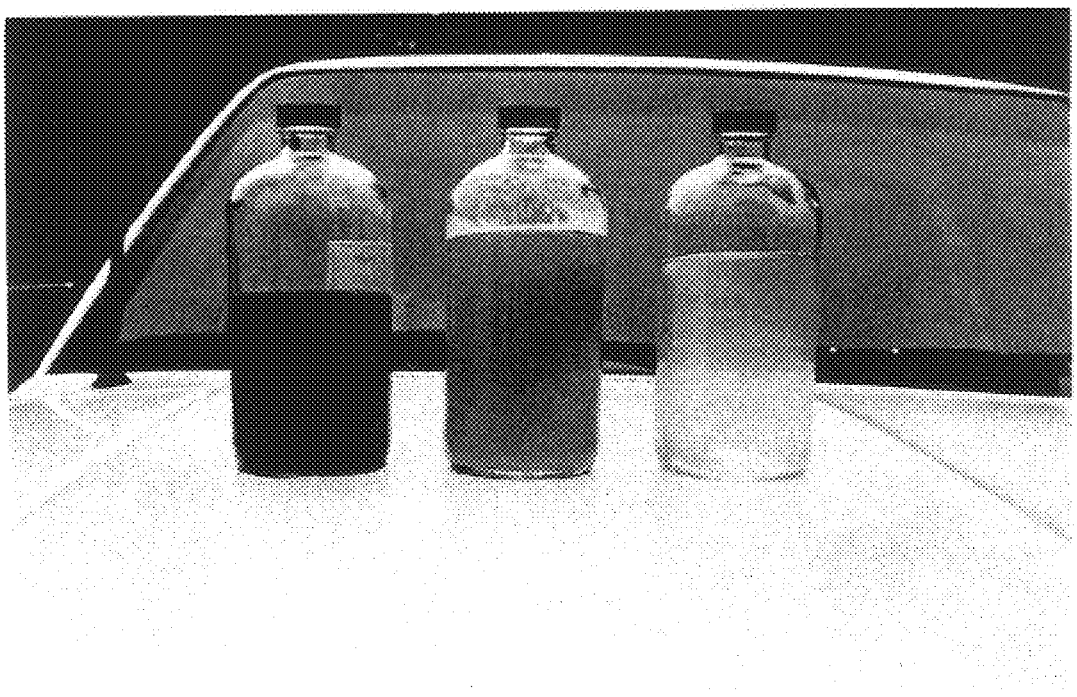
FIG. 4 is a color photograph showing qualitatively the degree of waste purification available from the method of the invention.

FIG. 4 shows qualitatively the degree of purification available from the method of the invention. In FIG. 4, bottle A shows a sample of the raw waste from Example 2. Bottle B shows a sample of the effluent of Example 2 after the first stage sedimentation tank 8. As can be seen, a large amount of MLSS have been removed after the first treatment stage 2. Bottle C shows a sample of effluent of Example 2 after the second stage sedimentation tank 12. As shown in bottle C, nearly all of the MLSS have been removed from the effluent after the second treatment stage 4.

The amounts of useable protein in the isolated purple non-sulfur bacterial consortium and the isolated Chlorella are shown in Table 6. Nutritional amounts of protein available in each biomass are deduced by subtracting the "protein equivalent" from the total protein percentage.

TABLE 6

Nutritional Amounts Of Protein Available In Biomasses

| | Total Protein (% wet) | Protein Equivalent (% wet) | Nutritional Protein (% wet) | % Moisture | Nutritional Protein (% Dry) |
|---|---|---|---|---|---|
| Purple Non-Sulfur Bacterial Consortium | 39.3 | 4.40 | 34.9 | 28.0 | 48.4 |
| Green algae (Chlorella) | 33.5 | 2.40 | 31.1 | 55.8 | 70.3 |

Example 3
Pilot Scale Photosynthetic Purification Process Using a Photobioreactor In this Example, a photosynthetic purification process was undertaken as described in Example 2 above, except that the first and second stage growth reactor tanks were each replaced by photobioreactors as described in U.S. Pat. No. 5,137,828. An anaerobic digester was used to treat the incoming waste as a preliminary step prior to processing through the photobioreactors. All other processing conditions remained the same. Results of this photosynthetic processing are shown below in Table 7.

TABLE 7

Capture Efficiencies for Photosynthetic Swine Waste Treatment using a Photobioreactor

| | Raw Waste (g/l) | 1st Stage Effluent (mg/l) | 2nd Stage Effluent (mg/l) | 1st Stage Removal Eff. (%) | 2nd Stage Removal Eff. (%) | Overall Removal Eff. (%) |
|---|---|---|---|---|---|---|
| Solids | 80,000 | 45,000 | 5–50 | 44.00 | 99.9 | 99.9 |
| BOD | 70,000 | 15,000 | 5–75 | 78.6 | 99.7 | 99.9 |
| $NH_3$—N | 3,000 | 2,500 | 2–100 | 16.6 | 98.0 | 98.3 |
| Total P-P | 400 | 400 | 2–10 | 0 | 98.5 | 98.5 |

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents, patent applications, and publications mentioned are herein incorporated by reference in their entireties.

What is claimed is:

1. A method for treating a waste stream containing organic and inorganic wastes, comprising the steps of:
    (a) contacting a waste stream comprising organic and inorganic wastes with a first mixture of microorganisms comprising one or more photosynthetic prokaryotic organisms under controlled process conditions and in the presence of light in at least one first reaction vessel, said first reaction vessel in fluid communication with at least one first photobioreactor, wherein a first portion of said wastes is assimilated by said first mixture of microorganisms to produce a partially purified waste stream comprising said first mixture of microorganisms and a second portion of said wastes;
    (b) removing said first mixture of microorganisms from said partially purified waste stream to produce an isolated first mixture of microorganisms and a partially purified effluent stream containing said second portion of said wastes;
    (c) transferring said partially purified effluent stream from said at least one first reaction vessel to at least one second reaction vessel;
    (d) contacting said partially purified effluent stream with a second mixture of microorganisms comprising algae under controlled process conditions and in the presence of light in said at least one second reaction vessel, said second reaction vessel in fluid communication with at least one second photobioreactor, wherein substantially all of said second portion of said wastes is assimilated by said second mixture of microorganisms to produce a substantially purified waste stream comprising said second mixture of microorganisms and a substantially purified effluent; and
    (e) removing said second mixture of microorganisms from said substantially purified waste stream to produce an isolated second mixture of microorganisms and said substantially purified effluent.

2. The method of claim 1, wherein said waste stream comprises animal waste.

3. The method of claim 1, wherein said organic and inorganic wastes comprise carbon sources, nitrogen sources, oxygen sources, phosphorous sources, and combinations thereof.

4. The method of claim 1, wherein said one or more photosynthetic prokaryotic organisms are purple non-sulfur bacteria.

5. The method of claim 4, wherein said purple non-sulfur bacteria are selected from the group consisting of Rhodospirillum, Rhodopseudomonas, Rhodobacter, Chromatium, Rubrivivax, and combinations thereof.

6. The method of claim 1, wherein said removing step (b) further comprises the step of adding a polymer coagulant to said partially purified waste stream.

7. The method of claim 1, wherein said removing step (b) is accomplished by gravity sedimentation.

8. The method of claim 1, wherein said removing step (b) is accomplished by centrifugation.

9. The method of claim 1, wherein said isolated first mixture of microorganisms are further processed into animal feed.

10. The method of claim 1, wherein said algae are selected from the group consisting of Pyrrhophyta, Heterokontophyta, Chlorophyta, Euglenophyta, cyanobacteria (blue-green algae), and combinations thereof.

11. The method of claim 10, wherein said Chlorophyta are selected from the group consisting of Chlorella, Scenedesmus, Oocystis, Euglena, and combinations thereof.

12. The method of claim 10, wherein said cyanobacteria are selected from the group consisting of Spirulina, Oscillatoria, Phormidium, and combinations thereof.

13. The method of claim 1, wherein said removing step (e) further comprises the step of adding a polymer coagulant to said substantially purified waste stream.

14. The method of claim 1, wherein said removing step (e) is accomplished by gravity sedimentation.

15. The method of claim 1, wherein said removing step (e) is accomplished by centrifugation.

16. The method of claim 1, wherein said isolated second mixture of microorganisms is further processed into animal feed.

17. The method of claim 1, wherein said substantially purified effluent is recycled to said first reaction vessel.

18. The method of claim 1, wherein said at least one first reaction vessel and said at least one second reaction vessel are independently photobioreactors.

19. The method of claim 18, wherein said photobioreactors each comprise:

an upstanding core structure comprising a solid or open framework;

a transparent tube wound on said core structure wherein the exterior of said transparent tube wound on said core structure is exposed to light; and means to encourage light penetration into said tube in the region of contact between said tube and said core structure.

20. The method of claim 1, wherein said algae are selected from the group consisting of unicellular algae species and filamentous algae species.

21. A method for treating a waste stream containing organic and inorganic wastes, comprising the steps of:

(a) contacting a waste stream comprising organic and inorganic wastes with a first mixture of microorganisms comprising one or more photosynthetic prokaryotic organisms under controlled process conditions and in the presence of light in at least one first photobioreactor, wherein a first portion of said wastes is assimilated by said first mixture of microorganisms to produce a partially purified waste stream comprising said first mixture of microorganisms and a second portion of said wastes;

(b) removing said first mixture of microorganisms from said partially purified waste stream to produce an isolated first mixture of microorganisms and a partially purified effluent stream containing said second portion of said wastes;

(c) transferring said partially purified effluent stream from said at least one first photobioreactor to at least one second photobioreactor;

(d) contacting said partially purified effluent stream with a second mixture of microorganisms comprising algae under controlled process conditions and in the presence of light in said at least one second photobioreactor, wherein substantially all of said second portion of said wastes is assimilated by said second mixture of microorganisms to produce a substantially purified waste stream comprising said second mixture of microorganisms and a substantially purified effluent; and (e) removing said second mixture of microorganisms from said substantially purified waste stream to produce an isolated second mixture of microorganisms and said substantially purified effluent.

22. The method of claim 21, wherein said waste stream comprises animal waste.

23. The method of claim 21, wherein said organic and inorganic wastes comprise carbon sources, nitrogen sources, oxygen sources, phosphorous sources, and combinations thereof.

24. The method of claim 21, wherein said one or more photosynthetic prokaryotic organisms are purple non-sulfur bacteria.

25. The method of claim 24, wherein said purple non-sulfur bacteria are selected from the group consisting of Rhodospirillum, Rhodopseudomonas, Rhodobacter, Chromatium, Rubrivivax, and combinations thereof.

26. The method of claim 21, wherein said removing step (b) further comprises the step of adding a polymer coagulant to said partially purified waste stream.

27. The method of claim 21, wherein said removing step (b) is accomplished by gravity sedimentation.

28. The method of claim 21, wherein said removing step (b) is accomplished by centrifugation.

29. The method of claim 21, wherein said isolated first mixture of microorganisms are further processed into animal feed.

30. The method of claim 21, wherein said algae are selected from the group consisting of Pyrrhophyta, Heterokontophyta, Chlorophyta, Euglenophyta, cyanobacteria (blue-green algae), and combinations thereof.

31. The method of claim 30, wherein said Chlorophyta are selected from the group consisting of Chlorella, Scenedesmus, Oocystis, Euglena, and combinations thereof.

32. The method of claim 30, wherein said cyanobacteria are selected from the group consisting of Spirulina, Oscillatoria, Phormidium, and combinations thereof.

33. The method of claim 21, wherein said removing step (e) further comprises the step of adding a polymer coagulant to said substantially purified waste stream.

34. The method of claim 21, wherein said removing step (e) is accomplished by gravity sedimentation.

35. The method of claim 21, wherein said removing step (e) is accomplished by centrifugation.

36. The method of claim 21, wherein said isolated second mixture of microorganisms is further processed into animal feed.

37. The method of claim 21, wherein said substantially purified effluent is recycled to said first photobioreactor.

38. The method of claim 21, wherein said first and said second photobioreactors each comprise:

an upstanding core structure comprising a solid or open framework;

a transparent tube wound on said upstanding core structure wherein the exterior of said substantially transparent tube wound on said upstanding core structure is exposed to light; and means to encourage light penetration into said tube in the region of contact between said tube and said core structure.

39. The method of claim 21, wherein said algae are selected from the group consisting of unicellular algae species and filamentous algae species.

* * * * *